United States Patent
Dehlinger et al.

(10) Patent No.: US 8,900,434 B2
(45) Date of Patent: Dec. 2, 2014

(54) THREE DIMENSIONAL MICROELECTRODE SYSTEM FOR DIELECTROPHORESIS

(71) Applicant: Lawrence Livermore National Security, LLC, Livewrmore, CA (US)

(72) Inventors: Dietrich A. Dehlinger, Dublin, CA (US); Klint A. Rose, Alviso, CA (US); Maxim Shusteff, Oakland, CA (US); Christopher G. Bailey, Pleasanton, CA (US); Raymond P. Mariella, Jr., Danville, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 0 days.

(21) Appl. No.: 13/945,768

(22) Filed: Jul. 18, 2013

(65) Prior Publication Data

US 2013/0306481 A1 Nov. 21, 2013

Related U.S. Application Data

(62) Division of application No. 12/843,269, filed on Jul. 26, 2010, now Pat. No. 8,524,064.

(60) Provisional application No. 61/326,714, filed on Apr. 22, 2010.

(51) Int. Cl.
| | |
|---|---|
| *G01N 27/447* | (2006.01) |
| *G01N 27/26* | (2006.01) |
| *B03C 5/02* | (2006.01) |
| *B01D 57/02* | (2006.01) |
| *B03C 5/00* | (2006.01) |

(52) U.S. Cl.
CPC .............. *B03C 5/005* (2013.01); *G01N 27/447* (2013.01); *B01L 2400/0424* (2013.01); *B03C 5/026* (2013.01)
USPC ............ 204/547; 204/643; 204/400; 204/600

(58) Field of Classification Search
CPC .................... B03C 5/00–5/028; G01N 27/221; G01N 27/447; B01L 2400/0424
USPC .......................... 204/547, 600–647, 450, 400
See application file for complete search history.

(56) References Cited

U.S. PATENT DOCUMENTS

| | | | |
|---|---|---|---|
| 6,352,838 | B1 | 3/2002 | Krulevitch et al. |
| 6,730,204 | B2 | 5/2004 | Mariella, Jr. |
| 6,761,811 | B2 | 7/2004 | Mariella, Jr. |
| 2002/0139675 | A1* | 10/2002 | Mariella, Jr. .................. 204/547 |
| 2007/0125650 | A1* | 6/2007 | Scurati et al. ................. 204/547 |

FOREIGN PATENT DOCUMENTS

WO   WO 2007/059194   *   5/2007

* cited by examiner

*Primary Examiner* — Jennifer Dieterle
(74) *Attorney, Agent, or Firm* — Eddie E. Scott

(57) ABSTRACT

A dielectrophoresis method for separating particles from a sample, including a dielectrophoresis channel, the dielectrophoresis channel having a central axis, a bottom, a top, a first side, and a second side; a first mesa projecting into the dielectrophoresis channel from the bottom and extending from the first side across the dielectrophoresis channel to the second side, the first mesa extending at an angle to the central axis of the dielectrophoresis channel; a second mesa projecting into the dielectrophoresis channel from the bottom and extending from the first side across the dielectrophoresis channel to the second side, the second mesa parallel to said first mesa; a space between at least one of the first electrode and the second side or the second electrode and the second side; and a gap between the first electrode and the second electrode, and pumping a recovery fluid through said gap between said first electrode and into said space between at least one of said first mesa and said second side or said second mesa and said second side.

3 Claims, 8 Drawing Sheets

THREE DIMENSIONAL MICROELECTRODE SYSTEM FOR DIELECTROPHORESIS

CROSS-REFERENCE TO RELATED APPLICATIONS

This application is a Divisional of U.S. patent application Ser. No. 12/843,269, filed Jul. 26, 2010, entitled "Three Dimensional Microelectrode System For Dielectrophoresis" now U.S. Pat. No. 8,524,064, which claims the benefit under 35 U.S.C. §119(e) of U.S. Provisional Patent Application No. 61/326,714 filed Apr. 22, 2010 entitled "3D microelectrode system for dielectrophoresis," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to dielectrophoresis and more particularly to a three dimensional microelectrode system for dielectrophoresis.

2. State of Technology

Dielectrophoresis (DEP) is a force that is proportional both to the volume of objects/particles and to the gradients of electric potential energy on those objects/particles. For a spherical particle of radius r, the force on the particle in a fluid medium depends on the Clausius-Mossotti factor (CM); a ratio of the conductivities and permittivities of the surrounding medium and the particle itself. The direction of the force depends on the sign of the CM and can change sign as a function of the electric field frequency. When the CM is positive, particles will be attracted to regions of relatively high electric field (known as positive DEP), and when the CM is negative, particles will be repelled from regions of high electric field (negative DEP), with the force being proportional to the local gradient of the electric potential energy.

DEP has been used to extensively study the material properties of biological samples, the force exhibited by swimming bacteria, and as a method for particle separation. With few exceptions. DEP has been performed on samples with low surrounding medium conductivity ($10^{-5}$-$10^{-4}$ mS/cm). There are many reasons for this, with varying degrees of importance. At higher conductivity, the CM is almost always negative, which makes separation based on the sign of the CM impossible, as all particles will travel away from regions of high electric field. Additionally, applying electric fields through highly conductive media can lead to several extremely disruptive effects, such as solution joule heating, bubbling from electrolysis, loss of voltage over the electric double layer, and the degradation of the electrodes used to drive the field gradients. Finally, the increased solution conductivity can reduce the resistance of the DEP system, which can lead to a significant loss of voltage in the region of interest as a greater portion of the voltage is dropped over the wires leading to the electrodes or power supply itself due to its internal resistance. Since the DEP force scales with the square of the electric field, reducing the effective voltage due to these system losses reduces the force on particles. However, many biological samples of interest naturally possess solution conductivities between 1 and 20 mS/cm, meaning that for DEP to be effectively applied to these samples in traditional systems there must either be a dilution or other sample processing step. This can lead to damage of the biological particles of interest, either due to mechanical reasons, or due to the loss of osmotic pressure from the lowered solution conductivity. Additionally, these processes require some degree of sample handling which increases time, cost, and required operator skill level in a laboratory or clinical environment. Ideally, Applicants would like to have a sample analysis system that is minimally disruptive to cell populations, and can be done in an automated format with little to no preparation.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides high-throughput sample preparation of biological material. It separates out cells from a background solution containing other biological materials (viruses, proteins, RNA, DNA, etc) in order to allow uncontaminated analysis of either the background materials or the cells. The present invention utilizes dielectrophoretic forces to trap cells in solution against a fluid flow. As opposed to traditional dielectrophoresis systems, the present invention simultaneously works with small particles (minimum size 0.5 µm), high conductivity solutions (20 mS/cm), and high throughput (>10 µL/min).

The present invention provides a dielectrophoresis apparatus for separating particles from a sample, including an apparatus body; a dielectrophoresis channel in the apparatus body, the dielectrophoresis channel having a central axis, a bottom, a top, a first side, and a second side; a first mesa projecting into the dielectrophoresis channel from the bottom and extending from the first side across the dielectrophoresis channel to the second side, the first mesa extending at an angle to the central axis of the dielectrophoresis channel, a first electrode extending along the first mesa; a second mesa projecting into the dielectrophoresis channel from the bottom and extending from the first side across the dielectrophoresis channel to the second side, a second electrode extending along second first mesa, the second mesa extending at an angle to the central axis of the dielectrophoresis channel, a space between at least one of the first electrode and the second side or the second electrode and the second side, and a gap between the first electrode and the second electrode.

The present invention has use in sample preparation for medical countermeasures including triage and related scenarios, and for biological assays of environmental samples. The present invention also has use in medical/clinical assays, including point-of-care and field use. The present invention has use in quality control for food manufacturers. The present invention also has use in quality control for potable water.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1A:
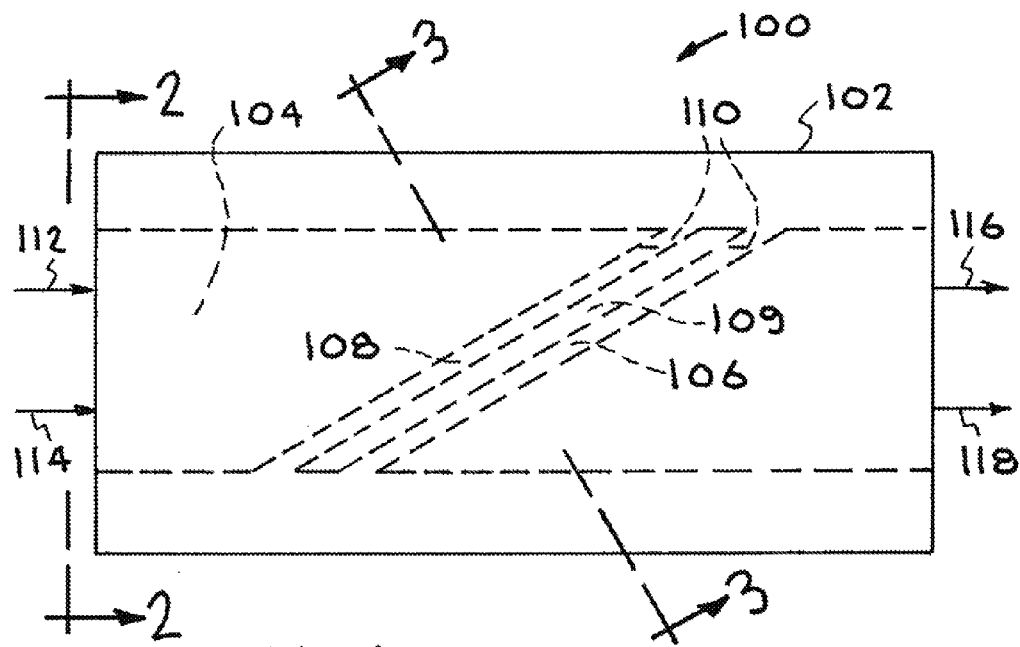
FIG. 1A is an illustration of one embodiment of the present invention showing a fluidic channel with and electrode pair.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 2:
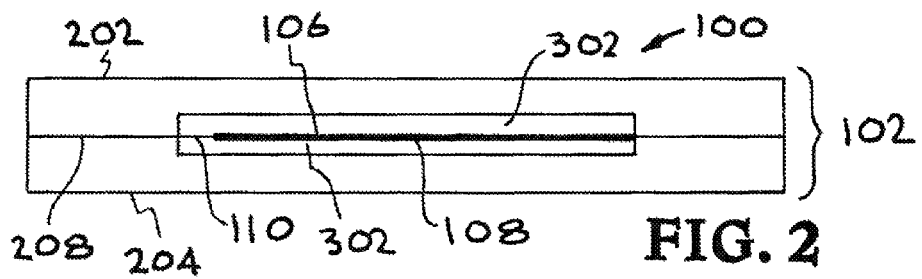
FIG. 2 is an end view of FIG. 1A.

Referring now to the drawing and in particular to FIG. 1A, one embodiment of a three dimensional microelectrode system for dielectrophoresis of the present invention is illustrated showing a fluidic channel with an electrode pair. The system is designated generally by the reference numeral 100. The system 100 provides a dielectrophoresis apparatus (DEP) for separating particles from a sample fluid. FIG. 1A is a top view of DEP apparatus 100. DEP apparatus 100 includes a chip assembly 102 made of a top and bottom parts, more clearly illustrated in FIG. 2. The top and bottom parts of chip assembly have DEP mesa (MESA) electrodes fabricated n their respective parts. The flow arrows 112, 114, 116 and 118 indicate that the recovery fluid 112 and input sample 114 enter the channel 104 at one end exit the other end as fractionated particles (particles of interest) 116 and pass-through particles 118.

Figure 1B:
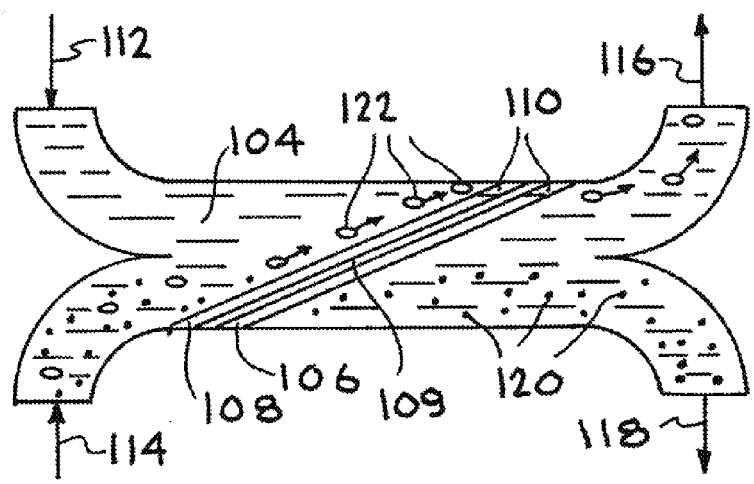
FIG. 1B is a schematic representation of FIG. 1A.

FIG. 1B is a schematic representation of the DEP apparatus 100 of FIG. 1A, FIG. 113 shows the recovery fluid 112 which can be water entering the channel 104. At the same time, the input sample 114 is also entering the channel 104. The input sample 114 could be but not limited to, for example blood. The input sample 114 will contain many varied particles and in the case illustrated in FIG. 18, the sample will also contain some particles on interest 122 shown here as small ovals. As the recovery fluid 112 and input sample 114 move through channel 104, they encounter the DEP electrodes 106 and 108.

The DEP electrodes 106 and 108 are composed of a metal, typically gold or platinum. They are connected to a signal generator located off the chip and are driven with an AC voltage. The frequency of the signal is high enough to prevent cell electroporation, suppress bubble formation due to electrolysis, and to be faster than the RC frequency of the system. Typical driving signals range from 5-20 Vpp and 0.5-10 MHz. Because of the low resistance of the device (<50 ohms) at the fluid conductivities of interest, the signal generator must be chosen such that it can provide the appropriate amount of power (around 1 W per cm of electrode pair). In addition, the electrodes are made wide and thick enough that they do not add a significant amount of resistance across their length.

Each electrode 106 and 108 is placed on a mesa 302 (see FIG. 3) raising it off the channel 104 surface, with one electrode running on the top side of the channel, and the other electrode on the bottom side. The heights of the mesas are typically equal to or slightly less than half the total channel height. The electrodes are generally parallel to each other, although they can be placed at a slight angle to generate particle fractionation along their length. The minimum spacing between electrodes ranges from sub-micron to remove nanometer-scale particle to 100's of µm to remove particles<100 µm. The total length of the electrodes is long, typically on the order of several cm, compared to the separation width, though this will vary with desired device parameters. The ridges run all the way across the channel, typically at very shallow angles to maximize the total electrode length. The electrodes run the length of the ridge, except on near the edge on one side of the channel where an electrode is cut short to form the gap 110 shown on FIGS. 1A and 1B. The gap 110 will eliminate the electric field in this region and allow the larger particles 122 to pass through.

The mesas 302 are a key feature of the design since they allow the DEP electrodes to be close together, but allow for the bulk of the fluid to travel through a much taller channel, minimizing the overall driving pressure.

Fluid is pumped down the channel and encounters the electrode/mesa pairs. Due to the geometry, the fluid path narrows, and the fluid is squeezed through the gap between the electrodes. Due to this constriction, all of the fluid passes within at most half the distance between the electrodes. Because of fluidic mass conservation, the flow velocity in the narrow gap is very low. The velocity is lowered because the cross-sectional area through the narrowed gap between the mesa is actually much larger than the area cross-section perpendicular to the original flow. The average fluid velocity is inversely proportional to the flow area, and thus the increased area leads to lowered fluid velocity. This is the case because the angle of the electrode is very low (a few degrees at most), and thus the length of the mesa is much greater than width of the channel. This increase in width is much greater than the loss in height due to the constriction between the mesas. For example, if the original cross-sectional area of the channel was A1=height*width, the area through the narrowed mesa region would be A2=(height/5)*(width*50)=10*A1. This low velocity is a key feature of the device, as the device is designed to maximize fluid volumetric flow rate yet minimize the velocity at any point in the channel (and especially minimize the normal fluid velocity through the electrode region). Throughput can be increased simply by making the channel and electrode mesas longer.

Figure 4:
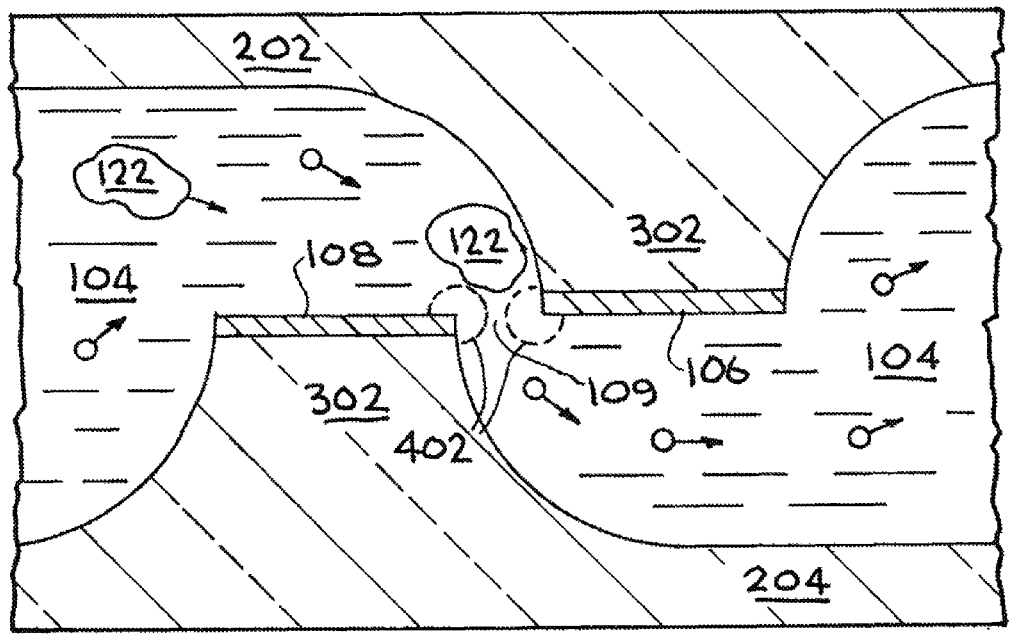
FIG. 4 is an enlarged view of the mesa electrodes.

The electrodes are run with an AC voltage sufficient to generate a DEP force such that the target size particles 122 and larger carried in the solution are repelled from the electrodes (see FIGS. 1B & 4). The device is functional when the net force of the fluid and DEP on a particle is zero in the perpendicular direction across the electrodes. The particles will flow down the channel until they reach a point where the DEP force balances out the fluidic force, at which point they will be held against the fluid flow. Because the overall flow is angled with respect to the electrodes, there will be a net force pushing the trapped particles 122 to one side of the fluid channel 104 and eventually through the region where one electrode ends short of the side wall and no DEP force is generated 110 (see FIG. 1B). The particles of interest 122 now leave the channel 104 and are collected as fractionated particles 116. The smaller particles 120 that have passed through the split 109 leave the channel 104 and are collected as pass-through particles 120.

Figure 3:
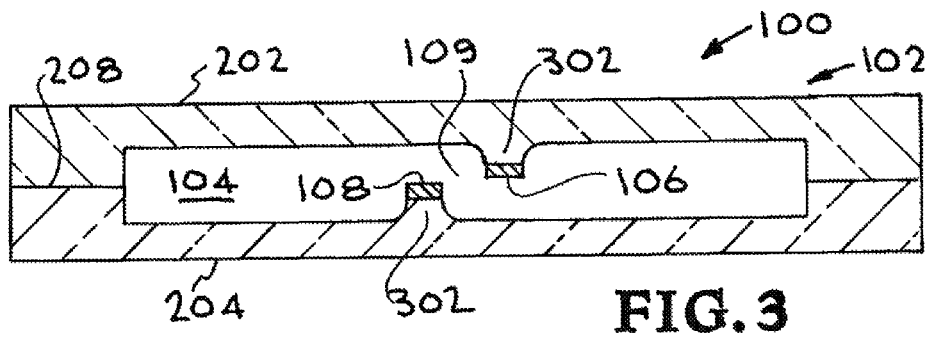
FIG. 3 is a cross section of FIG. 1A.

FIG. 4 is a greatly enlarged view of the area of the slit 109 between electrode 106 & 108 of FIG. 3. Here are shown the mesas 302 with the deposited electrode 106 and 108. As illustrated, the particles of interest 122 can physically pass through the slit 109 but are repelled by the electric fields generated by the electrodes 106 and 108. The electric field is shown as dashed circles labeled 402. The fields 402 urge the particles 122 to the side of channel 104 so as to pass through the non-field gap 110.

Figure 5:
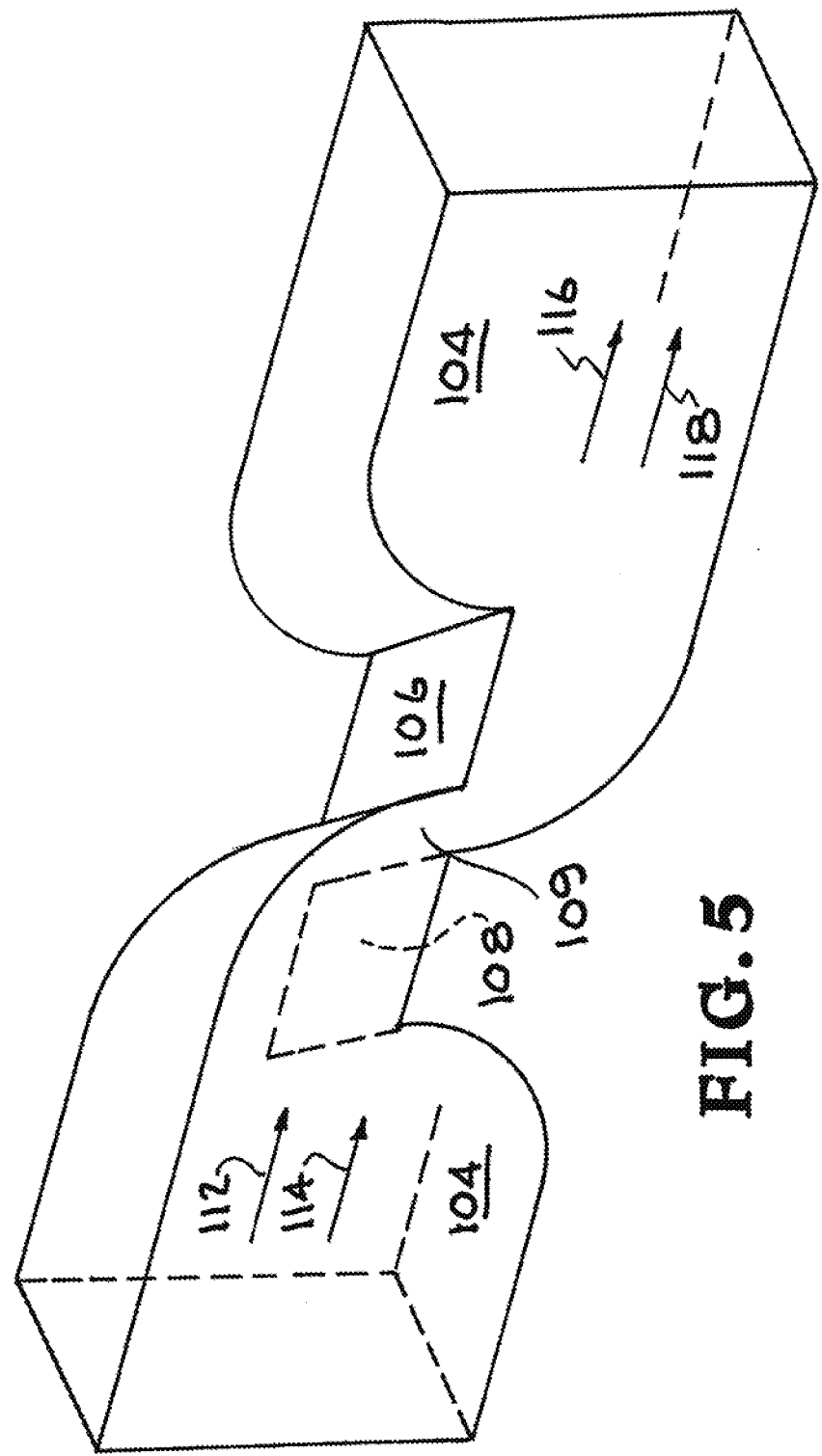
FIG. 5 is a cross section of the channel showing location of the electrodes.

FIG. 5 is a 3D cross section of channel 104 showing the location of the electrodes 106 and 108. This view also illustrates that the electrodes and their corresponding ridges are angled with respect to the rest of channel 104.

Figure 6A:
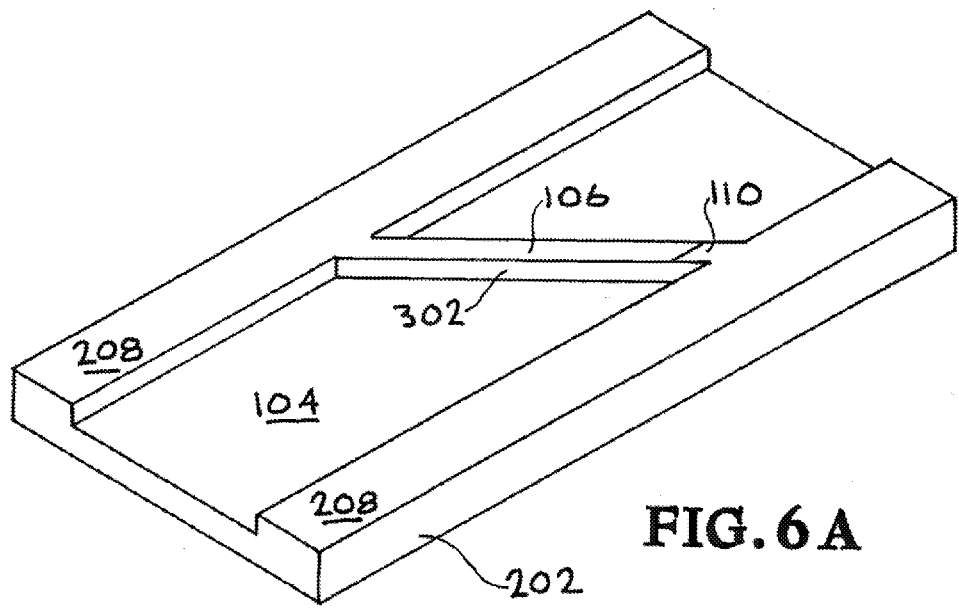
FIGS. 6A and 6B are illustrations of the two halves of device.

FIG. 6A shows the top half of chip assembly 102 flipped over to show DEP upper electrode 106 and mating surface 208.

Figure 6B:
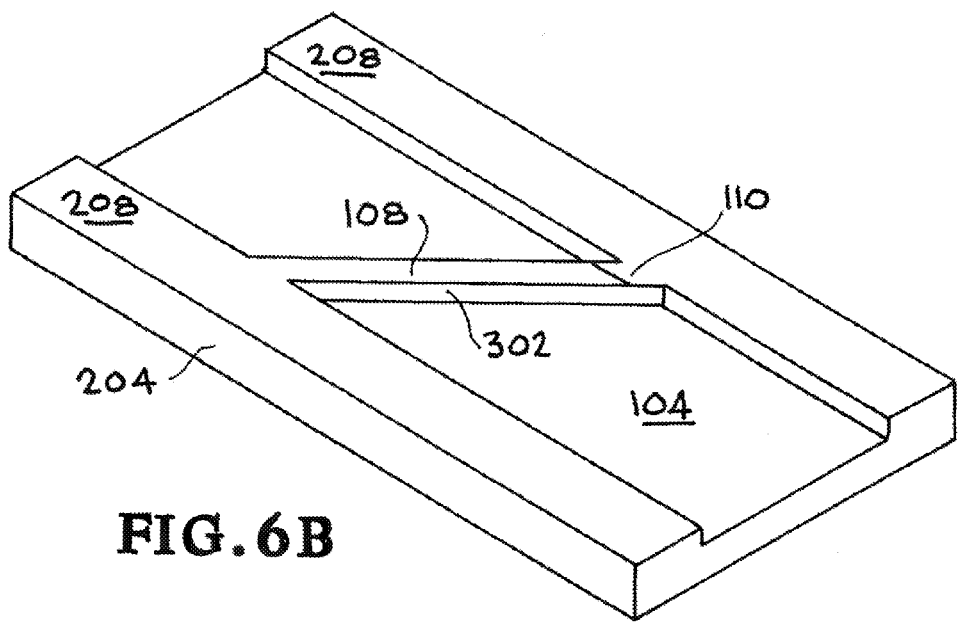

FIG. 6B is the bottom half of chip assembly 102 showing lower DEP electrode 108 and mating surface 208.

Figure 7:
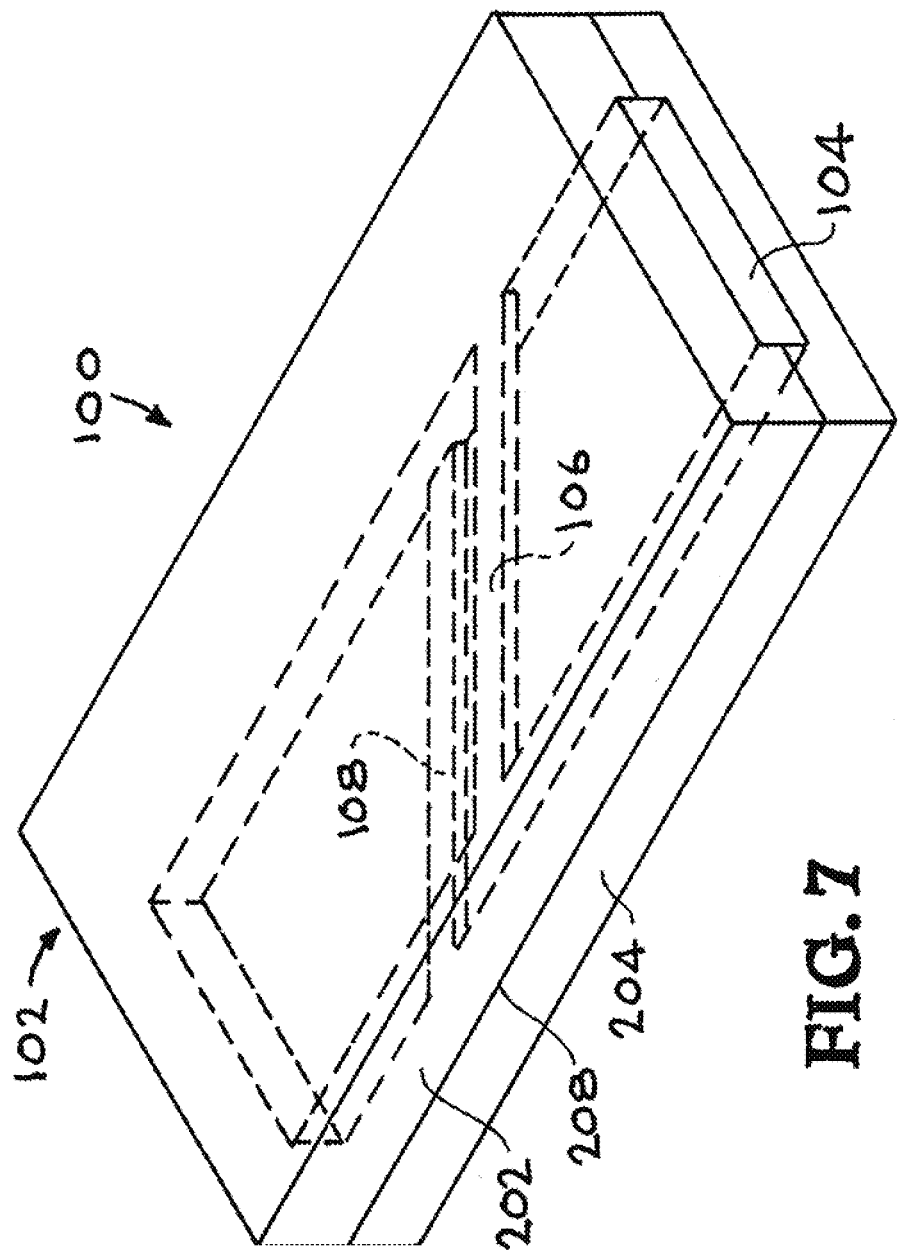
FIG. 7 is an illustration of an assembled device.

If you were to flip over upper half 202 and place on top of lower half 204 so that the mating surfaces 208 were adjacent and some bonding agent could be applied to the mating surface 208 to fabricate a monolithic structure 102 that would look like FIG. 7.

Figure 8:
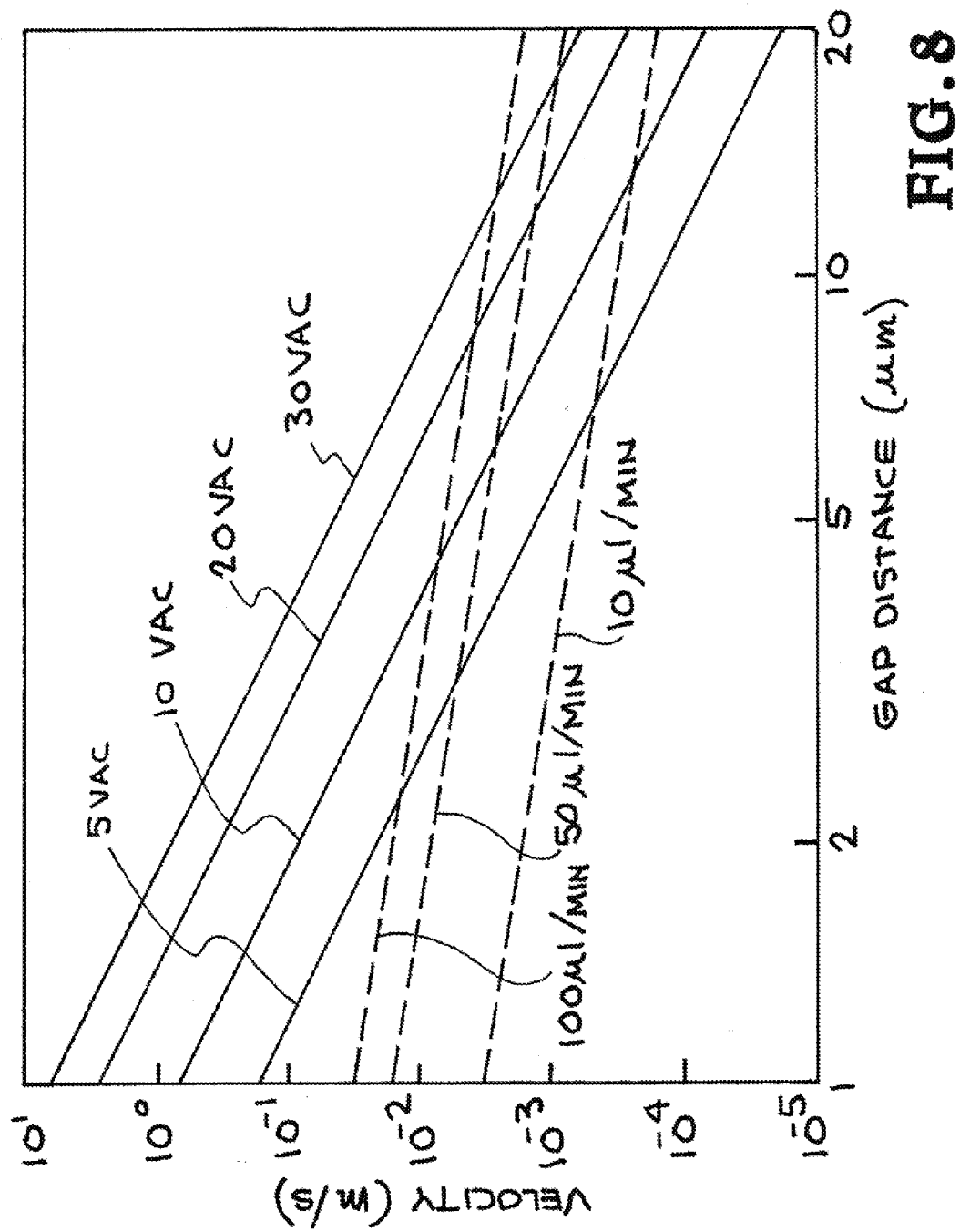
FIG. 8 is an example plot of device design parameters.

FIG. 8 is an example plot of device design parameters. The plot shown is the DEP stopping velocity a fluid flow for a 5 cm device. Solid lines are the maximum DEP induced velocities along a line halfway between the electrode where the force is the lowest, (see the slit 109 on FIG. 4) for 0.5 μm radius particles at various electrode spacing voltages. The dashed are the fluid volumetric flow rates through the slit 109. Successful device operation is when solid line is greater than the dashed line give device parameters (voltage, flow rate, slit size).

Figure 9A:
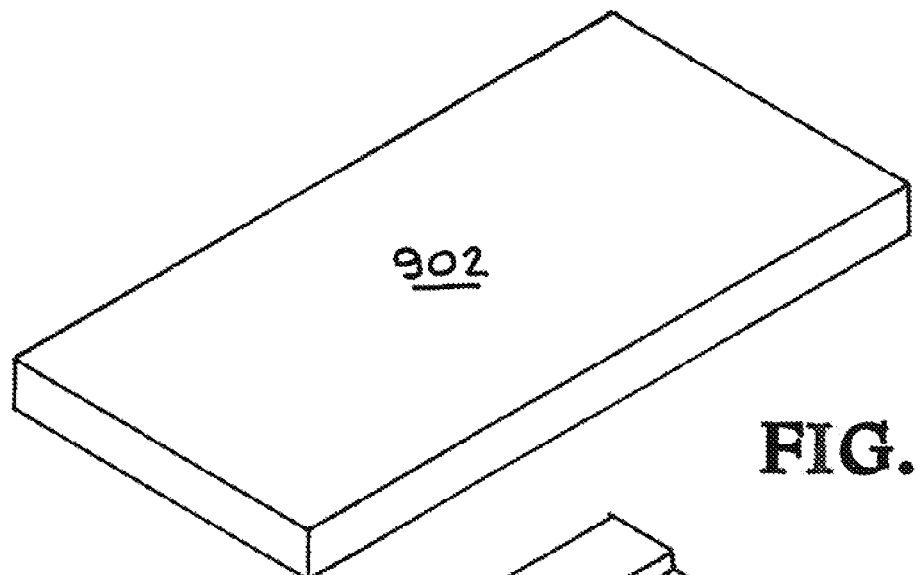
FIGS. 9A, 9B and 9C illustrate fabrication of the upper half of the device.

In FIGS. 9A, B, and C, we discuss the step in fabricating the chip assembly 102. FIG. 9A shows a block of material, examples of which are glass, silicon, plastic. The material used is not limited to the above listed materials.

Figure 9B:
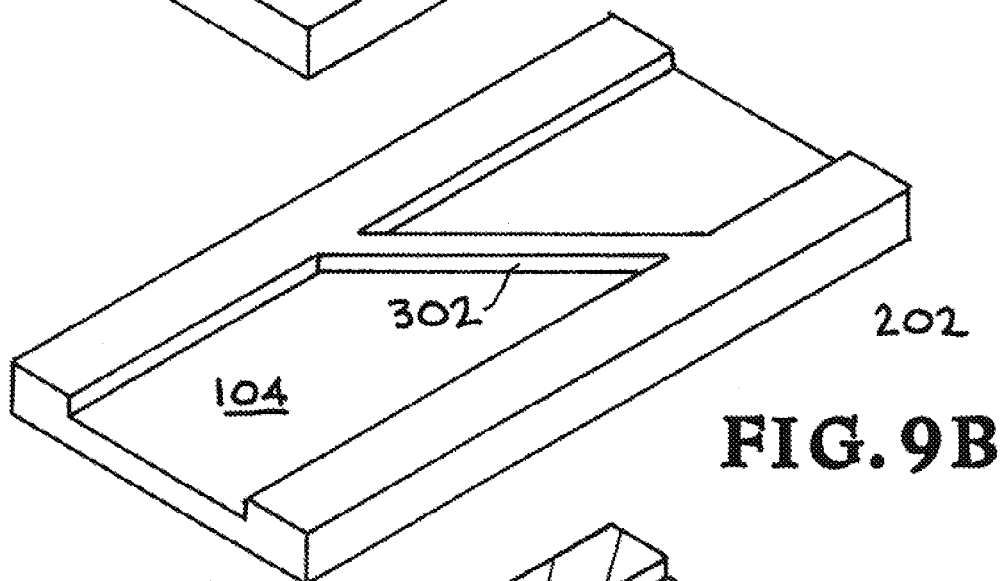

FIG. 9B shows the block of material of FIG. 9A after etching to form the channel 104 and mesa 302 (FIG. 3).

Figure 9C:
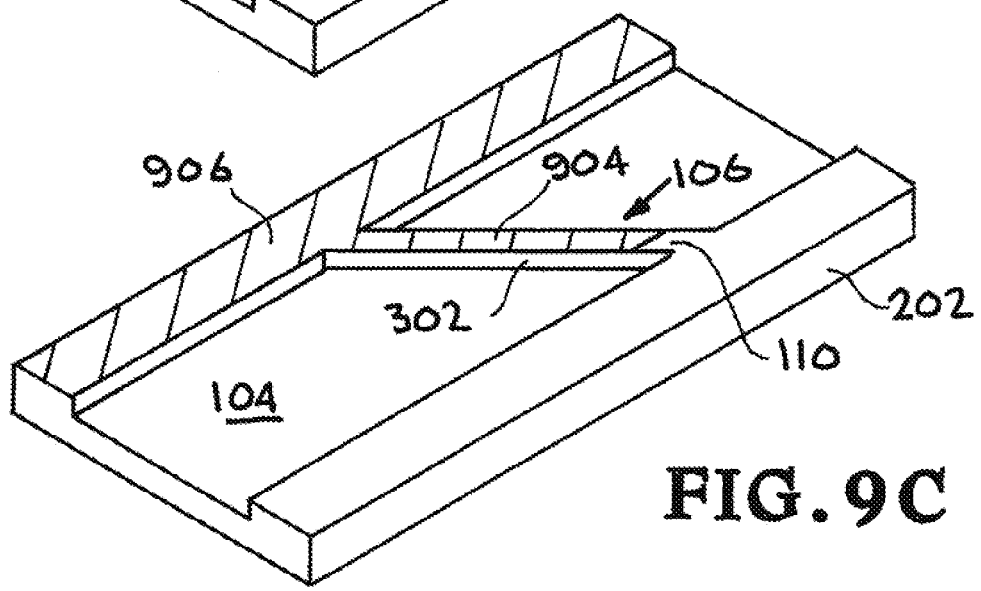
Figure 10A:
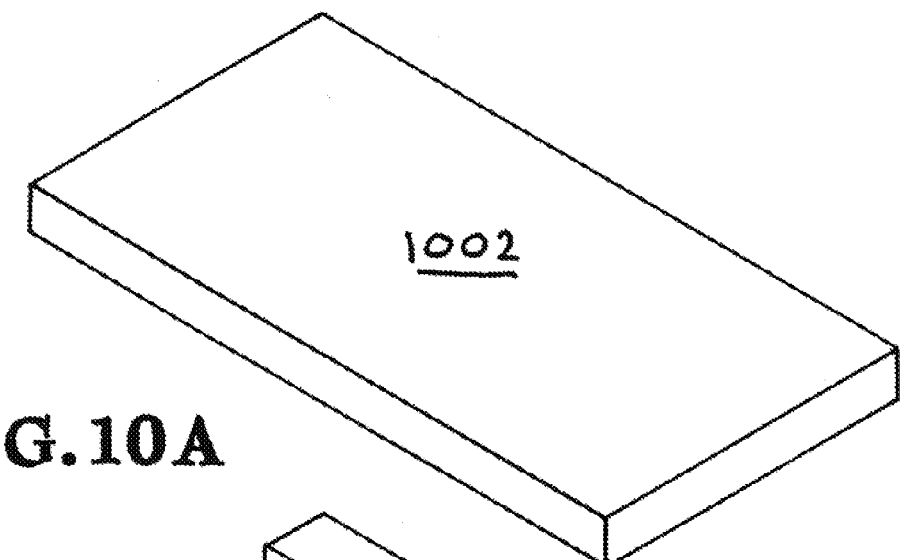
FIGS. 10A, 10B, and 10C illustrate fabrication of the lower half of the device.
Figure 10B:
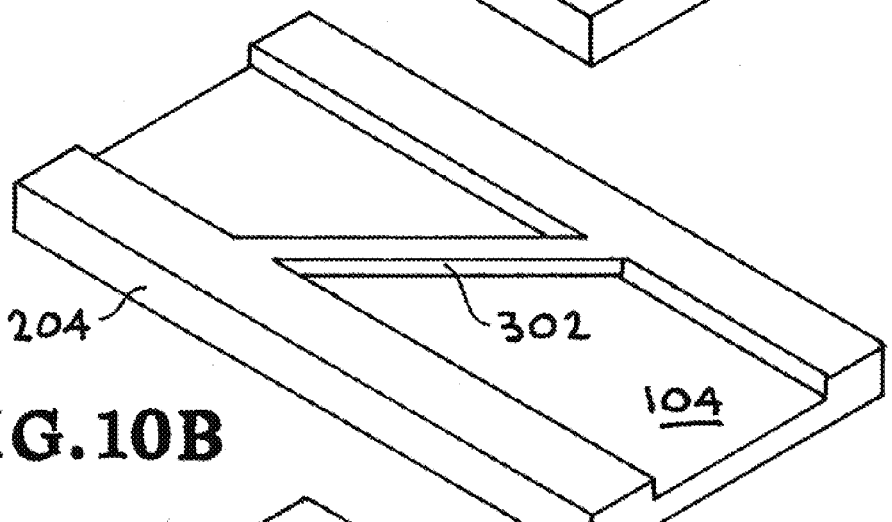
Figure 10C:
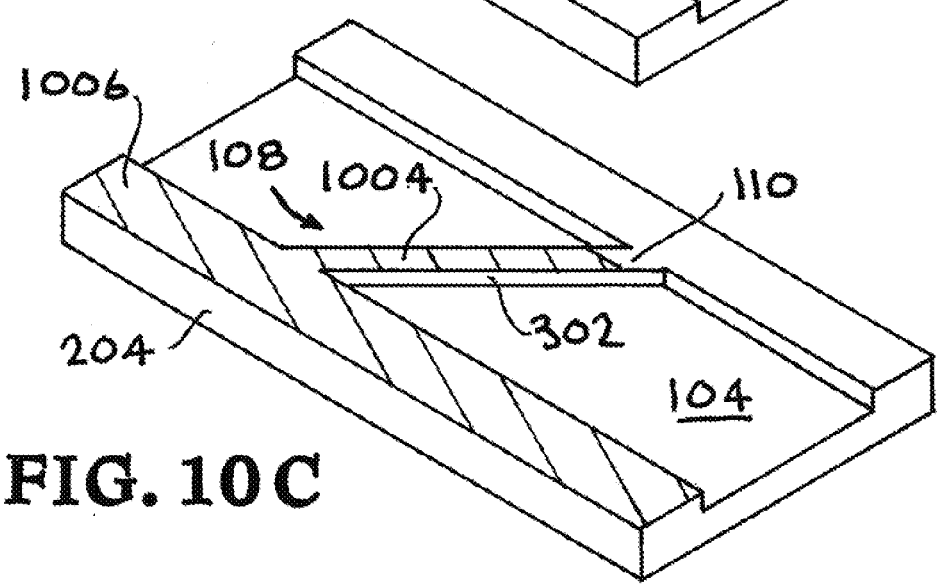

In FIG. 9C, a plating 904 composed of an inert metal, typically gold or platinum to the areas shown with cross hatching. This completes the upper and DEP mesa electrode 106. The plating labeled 906 can be used to connect electrode 106 to the signal generator located off the chip 102.

Here the block of material 1002 goes through the same steps as block 902 of FIG. 9A, B, C. The difference being that the electrode on mesa 302 does not extend the full width of channel 104. This forms the gap in the force field 110 discussed earlier. As in FIG. 9C, plating is deposited to complete DEP mesa electrode 108. Now we mate the two parts 202 and 204 as previously described for FIGS. 6A and 6B. We end up with the DEP apparatus of FIG. 7.

The system 100 uses a three-dimensional channel geometry that compresses the channel height in the regions of the electrodes and then expands out in all other regions to greatly reduce the overall fluidic resistance. Because of the reduction in channel height around the electrodes, all of the solution passes close to the regions of high DEP force, thus allowing the active manipulation of the entire solution as it passes past the electrode. Additionally, the short distances allow Applicants to reduce the total voltage so that unwanted electrochemical and electrothermal effects are minimized.

The present invention aims to bring together design parameters including:

High sample throughput (around 100 μl/min)
High sample conductivity (around 20 mS/cm)
Small particle size (minimum size around 0.5 μm)
Low pressure drop across system (<1 atm)
Maintain bacterial viability after processing The vast majority of DEP research has been done in conductivities at least 2 orders of magnitude below Applicants' target, instead focusing on the separation afforded by positive and negative DEP. The prior high-conductivity DEP work focuses on single-cell trapping, has low throughput, or has a very large particle-size threshold for separation.

The present invention works by utilizing dielectrophoresis (DEP) over very short length scales. The DEP force scales roughly as $1/r^3$ from the origin point (which are typically electrode edges or dielectric constrictions) where r is the particle radius. For any given point the terminal fluid velocity of a particle due to the DEP field is proportional to the square of particle radius and the square of the voltage applied. Thus if Applicants want to trap small particles, Applicants either need to use large voltages, or small distances. As mentioned, large voltages applied to solutions for the conductivities of interest causes several drawbacks, which render the device inoperable. Thus to provide a sufficient DEP force to trap small particles Applicants need to create very small electrode spacings. The straightforward solution would appear to be to use standard microfabrication techniques to place narrowly spaced electrodes across a microfluidic channel. However, this would imply that the entire channel would be of very narrow height, since typical channels have the same height all the way down their length. This in turn would lead to extremely high pressures required to drive the fluid through the system at the desired flow rates for reasonable channel geometries. Such designs exist in the literature, however their throughput is 1-2 orders of magnitude lower than Applicants' design. Applicants' invention addresses these overall problems in several ways. First, it uses a three-dimensional channel geometry that compresses the channel height in the regions of the electrodes and then expands out in all other regions to greatly reduce the overall fluidic resistance. Because of the reduction in channel height around the electrodes, all of the solution passes close to the regions of high DEP force, thus allowing the active manipulation of the entire solution as it passes past the electrode. Additionally, the short distances allow Applicants to reduce the total voltage so that unwanted electrochemical and electrothermal effects are minimized.

The present invention includes a pair of long electrodes running at an angle across a microfluidic channel. Each electrode is placed on a ridge (or mesa), raising it off of the channel surface, with one electrode running on the top side of the channel, and the other electrode on the bottom side. The heights of the mesas are typically equal to or slightly less than half the total channel height. The electrodes are generally parallel to each other, although they can be placed at a slight angle to generate particle fractionation along their length. The minimum spacing between electrodes ranges from sub-micron to remove nanometer-scale particle to 100's of µm to remove particles<100 µm. The total length of the electrodes is long, typically on the order of several cm, compared to the separation width, though this will vary with desired device parameters. The ridges run all the way across the channel, typically at very shallow angles to maximize the total electrode length. The electrodes run the length of the ridge, except near the edge on one side of the channel where an electrode is cut short to allow the larger particles to pass through. The mesas are the key feature of this design since they allow the DEP electrodes to be close together, but allow for the bulk of the fluid to travel through a much taller channel, minimizing the overall driving pressure.

Fluidics

Fluid is pumped down the channel and encounters the electrode/mesa pairs. Due to the geometry, the fluid path narrows, and the fluid is squeezed through the gap between the electrodes. Due to this constriction, all of the fluid passes within at most half the distance between the electrodes. Because of mass conservation and the incompressibility of the fluid, the flow velocity in the narrow gap is very low. The velocity is lowered because the cross-sectional area through the narrowed gap between the mesa is actually much larger than the area cross-section perpendicular to the original flow. For example if the original cross-sectional area of the channel was A1=height*width, the area through the narrowed mesa region might be something like A2=(height/5)*(width*50) =10*A1. This is the case because the angle of the electrode with respect to the channel is very low (a few degrees at most), and thus the length of the mesa is much greater than width of the channel. This increase in width is much greater than the loss in height due to the constriction between the mesas. The average fluid velocity is inversely proportional to the flow area, and thus the increased area leads to lowered fluid velocity. This low velocity is a key feature of the device, as the device is designed to maximize fluid volumetric flow rate yet minimize the velocity at any point in the channel (and especially minimize the normal fluid velocity through the electrode region). Throughput can be increased simply by making the channel and electrode mesas longer.

Electronics

The electrodes are composed of an inert metal, typically gold or platinum. They are connected to a signal generator located off the chip and are driven with an AC voltage. The frequency of the signal is enough to prevent cell electroporation, suppress bubble formation due to electrolysis, and to be faster than the RC frequency of the system. Typical driving signals range from 5-20 Vpp and 0.5-10 MHz. Because of the low resistance of the device (<50 ohms) at the fluid conductivities of interest, the signal generator must be chosen such that it can provide the appropriate amount of power (around 1 W per cm of electrode pair). In addition, the electrodes are made wide enough that they do not add a significant amount of resistance across their length.

Overall Operation

The electrodes are run with an AC voltage sufficient to generate a DEP force such that the target size particles (and larger) carried in the solution are repelled from the electrodes as illustrated in FIGS. 1B and 4. The device is functional when the net force of the fluid and DEP on a particle is zero in the perpendicular direction across the electrodes. The particles will flow down the channel until they reach a point where the DEP force balances out the fluidic force, at which point they will be held against the fluid flow as illustrated in FIGS. 1 and 4. Because the overall flow is angled with respect to the electrodes, there will be a net force pushing the trapped particles to one side of the fluid channel.

Alternate designs/considerations/operation

1) The gap is created not by horizontal separation of the mesas, but some degree of vertical separation
   a The height separation is caused by multiple downward etches into the substrate of varying amounts
   b The height separation is caused by a built up secondary layer
2) The channels are fabricated on glass wafers
3) The channels are fabricated on silicon wafers
4) The channels are fabricated out of plastic
5) The channels are fabricated out of a photo-patternable material
6) The channels are fabricated out of PDMS
7) The channels contain support pillars
8) The mesa is deposited after the channel has been etched
9) The mesa is wide compared to the channel depth
10) The mesa is narrow compared to the channel depth
11) The channel widens or narrows down its length
12) The channel height increases or decreases down its length
13) The mesa gap is taken to be large (20 µm or greater) for use on larger particles
14) The mesa gap is sub µm in order to manipulate very small particles
15) The device is used only for negative DEP
16) The device is used only for positive DEP
17) The DEP force is used in conjunction with fluidic forces
18) The DEP force is used in conjunction with acoustic forces
19) The DEP force is used in conjunction with AC-electroosmotic forces
20) The DEP force is used in conjunction with electroosmotic forces
21) The DEP force is used in conjunction with electrothermal forces
22) The DEP force is used in conjunction with electrophoretic forces
23) The DEP force is used in conjunction with optical forces
24) Local electrode driven DEP is used in conjunction with insulating DEP
25) The device is run at DC voltages
26) The device is run at frequencies below the RC time of the electrode/fluid system
27) The device is run at frequencies above the RC time of the electrode/fluid system
28) The device is run with multiple drive signals simultaneously
29) The device is used with a combination of negative and positive DEP
30) The device is used in low conductivity buffers
31) The device is used in high conductivity buffers
32) The input and output streams are different conductivities
33) The input and output streams are of different widths/flow rates
34) The electrode extends all the way across the channel
35) The electrode ends only part ways across the channel 36) The electrical system is monitored in order to analyze system information
   a. The monitoring is used to measure the size of the particle
   b. The monitoring is used to measure the position of the particle
   c. The monitoring is used to test fluid conductivity
   d. The monitoring is used to detect device clogging
   e. The monitoring is used to detect device degradation
37) The driving voltage is automatically tuned based on device conditions (conductivity, particle density, temperature)
38) The fluid flow is automatically tuned based on device conditions (conductivity, particle density, temperature)
39) The fractionated particles are removed by a channel on the input side of the mesa, rather than passing through it
40) The device is used solely as a filter with no collection of larger particles
41) There are multiple sets of mesas with different parameters (spacing, angle, voltage, etc) on the device to collect different
   populations of particle size
42) The electrode/mesas are shaped like a V in order to increase the device length
43) The channel and mesas are run in a serpentine pattern to increase device effective length
44) There are multiple channels run in parallel
45) The electrodes are angled slightly with respect to each other to allow different size thresholds for particles with respect to position across the channel/mesa length
46) The mesa only sticks out from one side of the channel
   a. The electrode on the flat side of the channel is wider than the mesa on the opposite side of the channel
   b. The electrode on the flat side of the channel is narrower than the mesa on the opposite side of the channel 47) The mesa changes height across the channel
48) The electrodes are made out of a nanostructured material
49) The electrodes are made out of a planar material or stacks of planar materials 50) The electrodes are made of a combination of planar and nanostructured materials
51) The electrode consists of layers of a combination of conductors of various heights, widths, and conductivities
52) The electrodes are transparent
53) The electrodes are made wholly or partially from a non metal conductor
54) The electrodes are made at least partially by doping the mesa to cause it to be conductive
55) The electrode is located only on the mesa
56) The electrode extends beyond the top of the mesa down into the channel
57) The device is actively cooled on one or both sides
58) The device is passively cooled on one or both sides
59) The fluid is cooled before entering the device
60) The input fluid is the output of a previous sample processing device
61) The output fluid flows into a subsequent device
62) The input fluid arrives directly from a living organism
63) The output fluid is placed in a living organism (for example used as part of a blood filter)

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A dielectrophoresis method for separating particles from a sample fluid containing the particles, comprising the steps of:
   providing a dielectrophoresis body
   providing a dielectrophoresis channel in said dielectrophoresis body, said dielectrophoresis channel having
   a central axis,
   a bottom,
   a top above said bottom,
   a first side, and
   a second side;
   providing a first mesa projecting into said dielectrophoresis channel from said bottom and extending from said first side across said dielectrophoresis channel to said second side, said first mesa extending at an angle to said central axis of said dielectrophoresis channel;
   providing a first electrode extending along said first mesa;
   providing a second mesa projecting from said top into said dielectrophoresis channel and extending from said first side across said dielectrophoresis channel to said second side, said second mesa parallel to said first mesa;
   providing a second electrode extending along said second mesa;
   providing a space between at least one of said first mesa and said second side or said second mesa and said second side; and
   providing a gap between said first electrode and said second electrode:
   providing a recovery fluid;
   pumping the sample fluid containing the particles into said dielectrophoresis channel so that the sample fluid containing the particles flows through said gap between said first electrode and said second electrode;
   pumping said recovery fluid into said dielectrophoresis channel along side the sample fluid containing the particles so that said recovery fluid flows through said gap between said first electrode and said second electrode and at least a portion of said recovery fluid flows into said space between at least one of said first mesa and said second side or said second mesa and said second side; and
   energizing said first electrode and said second electrode creating a dielectrophoresis on the particles causing the particles to move from the sample fluid to said recovery fluid thereby separating the particles from the sample fluid.

2. The dielectrophoresis method of claim 1 wherein the sample fluid and said recovery fluid move through said dielectrophoresis channel side by side and move through said dielectrophoresis channel in a laminar flow.

3. A dielectrophoresis method for separating particles from a sample fluid containing the particles, comprising the steps of:
   providing a dielectrophoresis body having a dielectrophoresis channel with
   a central axis,
   a bottom,
   a top above said bottom,
   a first side,
   a second side;
   a first mesa projecting into said dielectrophoresis channel from said bottom and extending from said first side across said dielectrophoresis channel to said second side, said first mesa extending at an angle to said central axis of said dielectrophoresis channel;
a first electrode extending along said first mesa;
a second mesa projecting from said top into said dielectrophoresis channel and extending from said first side across said dielectrophoresis channel to said second side, said second mesa parallel to said first mesa;
a second electrode extending along said second mesa;
a space between at least one of said first mesa and said second side or said second mesa and said second side; and
a gap between said first electrode and said second electrode:
pumping the sample fluid containing the particles into said dielectrophoresis channel so that the sample fluid containing the particles flows through said gap between said first electrode and said second electrode;
pumping a recovery fluid into said dielectrophoresis channel along side the sample fluid containing the particles so that said recovery fluid flows through said gap between said first electrode and said second electrode, wherein at least a portion of said recovery fluid moves through said dielectrophoresis channel proximate said space between at least one of said first electrode and said second side or said second electrode and said second side; and
energizing said first electrode and said second electrode creating a dielectrophoresis on the particles causing the particles to move from the sample fluid to said recovery fluid thereby separating the particles from the sample fluid.

* * * * *